United States Patent [19]

Summers et al.

[11] Patent Number: 5,023,328

[45] Date of Patent: Jun. 11, 1991

[54] LEPIDOPTERAN AKH SIGNAL SEQUENCE

[75] Inventors: Max D. Summers, Bryan; James Y. Bradfield; Larry L. Keeley, both of College Station, all of Tex.

[73] Assignee: The Texas A&M University System, College Station, Tex.

[21] Appl. No.: 389,377

[22] Filed: Aug. 4, 1989

[51] Int. Cl.$^5$ .................. C12N 15/16; C12N 15/12
[52] U.S. Cl. .................................. 536/27; 435/69.4
[58] Field of Search .............. 536/27; 435/172.3, 69.1, 435/69.4

[56] References Cited

U.S. PATENT DOCUMENTS 4,745,051  5/1988  Smith et al. .................. 435/320 X

OTHER PUBLICATIONS

Wolfe, S., *Biology of the Cell*, Wadsworth Pub. Co., Belmont, Calif., 1972, p. 263.
Watson, J. et al., *Recombinant DNA-A Short Course*, Scientific American Books, New York, 1983, pp. 3 and 38.
Suggs S. U. et al., 1981 *PNAS* 78(11)6613-6617.
Bradfield et al., "Adipokinetic Hormone Gene Sequence from Manduca sexta," The Journal of Biological Chemistry, vol. 264(22):12791-12793 (1989).
Schulz-Allen et al., "Synthesis of a Homodimer Neurohormone Precursor of Locust Adipokinetic Hormone Studied by In Vitro Translation and cDNA Cloning," Neuron, vol. 2:1369-1373 (1989).
Susumu Maeda, "Expression of Foreign Genes in Insects Using Baculovirus Vectors," Ann., Rev. Entomol., vol. 34:351-72 (1989).
Schaffer et al., "Cloning of Adipokinetic Hormone cDNA," Society for Neuroscience Abstracts, vol. 14(1):29, Abstract No. 17.4 (1988).
Schulz et al., "Molecular Biological Studies on the Synthesis of Locust Adipokinetic Hormones," Society of Neuroscience Abstracts, vol. 14 (1):29, Abstract No. 17.5 (1988).
Hekimi et al., "Identification and Purification of Two Precursors of the Insect Neuropeptide Adipokinetic Hormone," The Journal of Neuroscience, vol. 7(9):2773-2784 (1987).
Summers et al., "A Manual of Methods for Baculovirus Vectors and Insect Cell Culture Procedures," Texas Agriculture Experiment Station Bulletin No. 1555.
Keeley et al., "Speculations on Biotechnology Applications for Insect Neuroendocrine Research," Insect Biochem., vol. 17(5):639-651 (1987).
Ziegler et al., "Amine Acid Sequence of Manduca sexta Adipokinetic Hormone Elucidated by Combined Fast Atom Bombardment (FAB)/Tandem Mass Spectrometry," Biochemical and Biophysical Research Communications, vol. 133(1):337-342 (1985).

*Primary Examiner*—Richard A. Schwartz
*Attorney, Agent, or Firm*—Arnold, White & Durkee

[57] ABSTRACT

A baculovirus expression vector system is constructed wherein the natural signal DNA peptide sequence associated with the desired foreign gene, such as CD4 (T cell surface protein T4) is replaced by the signal DNA sequence from the Lepidopteran adipokinetic hormone (AKH) precursor signal peptides. The exemplary *Manduca sexta* AKH signal sequence is represented as follows:

5'... ATG—TAC—AAG—CTC—ACA—GTC—TTC—CTG—
ATG—TTC—
Met—Tyr—Lys—Leu—Thr—Val—Phe—Leu—Met—Phe—

ATC—GCT—TTC—GTC—ATC—ATC—GCT—GAG—
GCC... 3'
Ile—Ala—Phe—Val—Ile—Ile—Ala—Glu—Ala

3 Claims, 2 Drawing Sheets

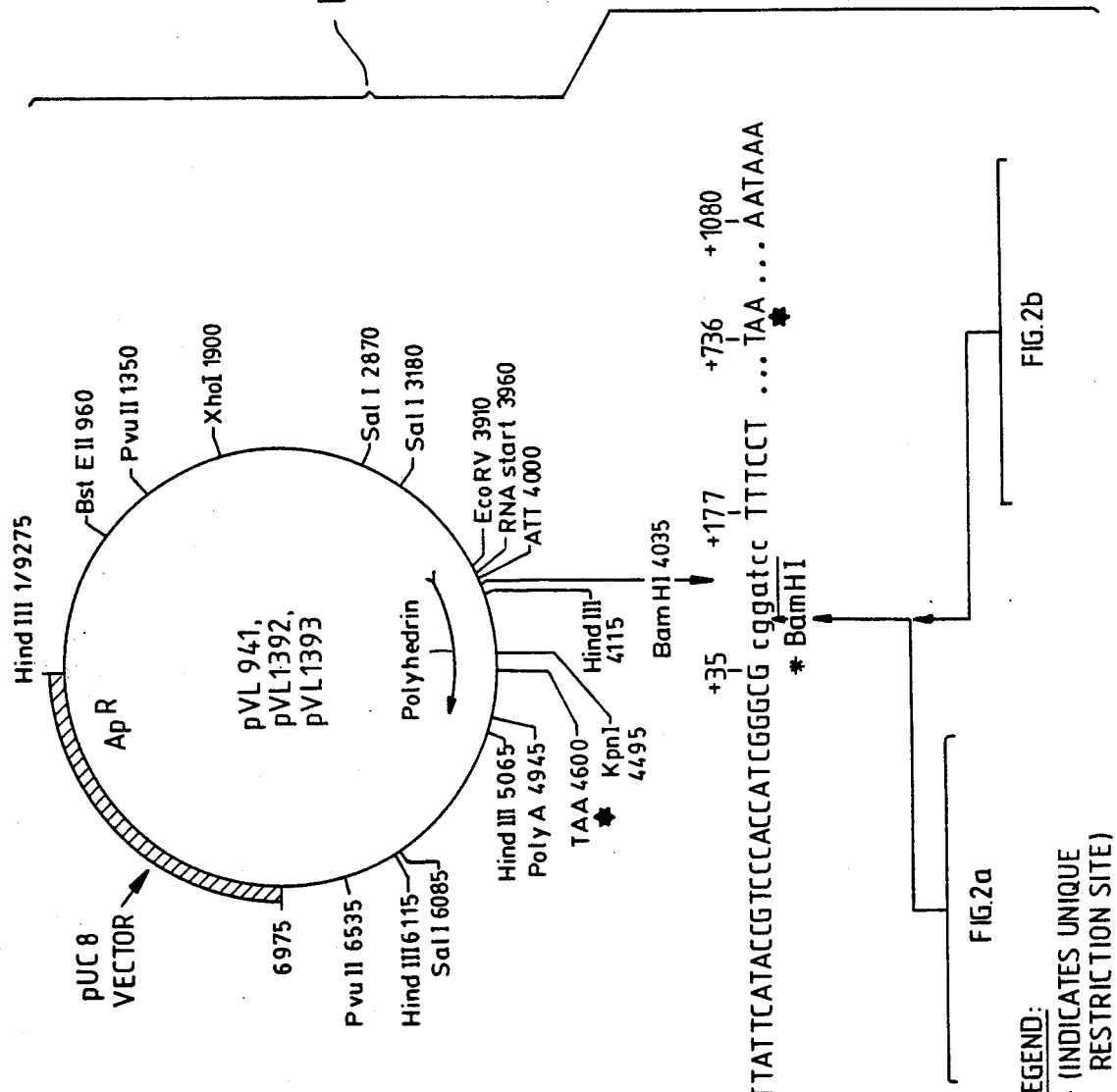

FIG. 2a pVL 1393

```
BamHI*
   XhoII
     AvaI
      XmaI*
       SmaI*
        HgiCI
         Asp718
          BanI
           KpnI
            XbaI*
             EcoRI*
                       BspMII
                             CfrI
                              GdiII
                               NotI*
                                XmaIII*
                                 NspBII
                                  BglII*
                                   PstI*
                                    XhoII gatcccgggtaccttctagaattccggagcggccgctgcagatct
ggcccatggaagatcttaaggcctcgccggcgacgtctagactag
```

FIG. 2b pVL 1392

```
   BglII*
    XhoII*
         NspBII
          PstI*
           CfrI
            GdiII
             NotI*
              XmaIII*
                        EcoRI*
                                   XbaI*
                                       Asp718
                                        BanI
                                         AvaI
                                          KpnI
                                           XmaI*
                                            SmaI*
                                             BamHI*
                                              XhoII gatcagatctgcagcggccgcttccagaattctagaaggtaccgg
tctagacgtcgccggcgaggtcttaagatctttccatgggccctag
```

LEGEND:

\* (INDICATES UNIQUE RESTRICTION SITE)

LEPIDOPTERAN AKH SIGNAL SEQUENCE

BACKGROUND OF THE INVENTION

A. Field of the Invention

The present invention relates to insect adipokinetic hormone signal sequences useful for promoting the processing and secretion of foreign proteins in insect systems.

B. Description of the Related Art

Baculovirus expression vectors (BEVs) have become extremely important tools for the expression of foreign genes, both for basic research and for the production of proteins with direct clinical applications in human and veterinary medicine (W. Doerfler, *Curr. Top. Microbiol. Immunol.*, 131:51–68 (1968); V. A. Luckow and M. D. Summers, *Bio/Technology*, 6:47–55 (1988a); L. K. Miller, *Annual Review of Microbiol.*, 42:177–199 (1988); M. D. Summers, *Curr. Communications in Molecular Biology*, Cold Spring Harbor Press, Cold Spring Harbor, N.Y. (1988)). BEVs are recombinant insect viruses in which the coding sequence for a chosen foreign gene has been inserted behind a baculovirus promoter in place of the viral gene, e.g., polyhedrin (G. E. Smith and M. D. Summers, U.S. Pat. No., 4,745,051, which is incorporated herein by reference).

Thus, baculoviruses have gained popularity as expression vectors because of the advantages presented above. The BEV system is currently being employed in over 700 laboratories for the overexpression and production of many different gene products. To date, more than 50 different genes have now been expressed by employing this system (V. A. Luckow and M. D. Summers, *Bio/Technology*, 6:47–55 (1988)).

The use of baculovirus vectors relies upon the host cells being derived from insects. The proteins expressed by the BEVs are, therefore, synthesized, modified and transported in host cells derived from insects. Most of the genes that have been inserted and produced in the baculovirus expression vector system have been derived from mammalian species.

At present, the only mode of achieving secretion of a foreign gene product in insect cells is by way of the foreign gene's native signal peptide. Because the foreign genes are usually from non-insect organisms, their signal sequences may be poorly recognized by insect cells, and hence, levels of expression may be suboptimal.

Heretofore, the efficiency of expression of foreign gene products seems to depend primarily on the characteristics of the foreign protein. On average, nuclear localized or non-structural proteins are most highly expressed, secreted proteins are intermediate, and integral membrane proteins are the least expressed. One factor generally affecting the efficiency of the production of foreign gene products in a heterologous host system is the presence of native signal sequences (also termed presequences, targeting signals, or leader sequences) associated with the foreign gene. The signal sequence is generally coded by a DNA sequence immediately following (5' to 3') the translation start site of the desired foreign gene.

The expression dependence on the type of signal sequence associated with a gene product can be represented by the following example: If a foreign gene is inserted at a site downstream from the translational start site of the baculovirus polyhedrin gene so as to produce a fusion protein (containing the N-terminus of the polyhedrin structural gene), the fused gene is highly expressed. But less expression is achieved when a foreign gene is inserted in a baculovirus expression vector immediately following the transcriptional start site and totally replacing the polyhedrin structural gene. Insertions into the region −50 to −1 significantly alter (reduce) steady state transcription which, in turn, reduces translation of the foreign gene product. Use of the pVL941 vector optimizes transcription of foreign genes to the level of the polyhedrin gene transcription. Even though the transcription of a foreign gene may be optional, optimal translation may vary because of several factors involving processing: signal peptide recognition, mRNA and ribosome binding, glycosylation, disulfide bond formation, sugar processing, oligomerization, for example.

The properties of the insect signal peptide are expected to be more optimal for the efficiency of the translation process in insect cells than those from vertebrate proteins. This phenomenon can generally be explained by the fact that proteins secreted from cells are synthesized as precursor molecules containing hydrophobic N-terminal signal peptides. The signal peptides direct transport of the select protein to its target membrane and are then cleaved by a peptidase on the membrane, such as the endoplasmic reticulum, when the protein passes through it.

While it has been recognized that the signal sequence associated with a foreign inserted mammalian gene is recognized by the insect cell system and cleaved at the correct sites, the present invention is premised on the use of an insect signal sequence instead of or together with the mammalian signal sequence so as to further enhance the expression of the foreign gene in the insect cell system.

SUMMARY OF THE INVENTION

In general and overall scope, the present invention provides a method for improving the efficiency of expression of foreign gene products in insect systems by replacing the natural signal sequence of the foreign gene with DNA sequences encoding an insect signal peptide.

As disclosed herein, an exemplary insect signal sequence is the sequence encoding for a Lepidopteran adipokinetic hormone (AKH) precursor peptide. The AKH family consists of short blocked neuropeptides that regulate energy substrate mobilization and metabolism in insects. The first structural determination of an AKH was made in 1976 when an AKH common to two locust species was defined. Since then more than a dozen neuropeptides similar to the locust AKH have been recognized. AKH family members from orders as diverse as Orthoptera, Lepidoptera, and Diptera have been described. The AKH family is one of the largest peptide families known. In a preferred embodiment, a DNA sequence coding for a Lepidopteran *Manduca sexta* AKH signal peptide was isolated and cloned.

This invention provides an isolated DNA sequence comprising a DNA sequence coding for a signal peptide for a Lepidopteran adipokinetic hormone precursor or for a peptide having substantially the same chemical composition, function and biological activity. Specifically, this DNA sequence is further defined as the following nucleotide sequence: ATG TAC AAG CTC ACA GTC TTC CTG ATG TTC ATC GCT TTC GTC ATC ATC GCT GAG GCC and allelic variations thereof.

BRIEF DESCRIPTION OF THE DRAWINGS

FIG. 1 depicts a restriction endonuclease map of pVL941, and its unique BamHI restriction site, pVL941 requires the insertion o foreign genes which contain translation initiation signals, pVL941 contains an additional 630 bp EcoRI/Xma III fragment present at position 6975.

FIG. 2a depicts a restriction endonuclease map of pVL1393, with its unique restriction sites indicated by asterisks (*). pVL1393 requires the insertion of foreign genes which contain translation initiation signals.

FIG. 2b depicts a restriction endonuclease map of pVL1392, with its unique restriction sites indicated by asterisks (*). pVL1392 requires the insertion of foreign genes which contain translation initiation signals.

DETAILED DESCRIPTION OF THE PREFERRED EMBODIMENTS

Deposit of Plasmids

The preferred transfer vector plasmid pVL941-AKH, containing the AKH signal, plus a coding sequence for the remainder of the AKH precurser was deposited with American Type Culture Collection (Rockville, Maryland) on July 27, 1989, and assigned accession number ATCC 40637.

Viral DNA

The baculovirus Autographa californica nuclear polyhedrosis virus (AcMNPV), used in the examples as the original source of viral DNA was isolated according to procedures described in G. E. Smith and M. D. Summers, *Virology*, 89:517-520 (1978) and G. E. Smith and M. D. Summers, *J. Virol.*, 39:125-137 (1981).

According to the preferred embodiment of this invention, a particular strain of AcMNPV, E2, utilized. However, those skilled in the art who have the benefit of this disclosure will recognize that other baculoviruses and other baculovirus strains may also be suitably utilized to obtain viral DNA. In particular, it is expected that at least the closely related and naturally occurring strains, *Trichoplusia ni* MNPV, *Rachiplusia ou* MNPV, *Galleria mellonella* MNPV and any plaque-purified strains such as the M3, R9, S1 and S3 strains of AcMNPV isolated and characterized in G. E. Smith and M. D. Summers, *J. Virol.*, 33:311-319 (1980), as well as *Bombyx mori* NPV (BmNPV) may be utilized to advantage. Further description of those and other strains are found in G. E. Smith and M. D. Summers, *Virol.*, 89:517-527 (1978).

Plasmid DNA

Plasmids pVL941, pVL1392, pVL1393, were prepared according to the methods described in M. D. Summers and G. E. Smith, *A Manual of Methods for Baculovirus Vectors and Insect Cell Culture Procedures*, Texas Agricultural Experiment Station Bulletin No. 1555, Texas A&M University (1987) ("Bulletin No. 1555"). (See also V. A. Luckow and M D. Summers, *Virol.*, 170:31-39 (1989)).

The DNA fragment comprising the entire open reading frame of the CD4 (T cell surface protein T4) gene used in the examples was isolated from the plasmid pT4B, which was obtained from Dr. R. Axel, Howard Hughes Medical Institute, Columbia University. See also P. Maddon et al., *Cell*, 42:93-104 (1985).

Insect Cell Lines

The *Spodoptera frugiperda* Sf9 cell line was obtained from American Type Culture Collection (Rockville, Md.) and is assigned accession number ATCC CRL 1711. See M. D. Summers and G. E. Smith, Bulletin No. 1555, supra. Those skilled in the art who have the benefit of this disclosure will recognize that other clonal derivatives of the Sf9 cell line as well as *Trichoplusia ni* and other insects such as the silkworm, *Bombyx mori*, or insect cell cultures derived therefrom can be used to advantage.

Cell Medium

The TNMFH medium used in the examples was prepared according to the methods of M. D. Summers and G. E. Smith, Bulletin No. 1555, supra. (See also W. F. Hink, *Nature (London)*, 226:466-467 (1970)). The fetal calf serum used to supplement the TNMFH medium can be obtained from Hazelton Research Products, Inc. (Lenexa, Kan.).

Methods

Although the methodology described below is believed to contain sufficient detail to enable one skilled in the art to practice the present invention, the plasmids can be constructed and purified using standard recombinant DNA techniques described in T. Maniatis, E. F. Fritsch and J. Sambrook, *Molecular Cloning: A Laboratory Manual*, Cold Spring Harbor Laboratory (1982) under the current regulations described in United States Dept. of HEW, *National Institute of Health (NIH) Guidelines for Recombinant DNA Research*. These references include procedures for the following standard methods: cloning procedures with *E. coli* plasmids, transformation of *E. coli* cells, plasmid DNA purification, phenol extraction of DNA, ethanol precipitation of DNA, agarose gel electrophoresis, purification of DNA fragments from agarose gels, and restriction endonuclease and other DNA-modifying enzyme reactions. Accordingly, these available references are incorporated herein by reference.

The standard methods of insect cell culture, co-transfection and preparation of plasmids in accordance with the examples, are set forth in M. D. Summers and G. E. Smith, *A Manual of Methods for Baculovirus Vectors and Insect Cell Culture Procedures*, Texas Agricultural Experiment Station Bulletin No. 1555, Texas A&M University (1987). This reference also pertains to the standard methods of cloning genes into AcMNPV transfer vectors, plasmid DNA isolation, transferring genes into the AcMNPV genome, viral DNA purification, radiolabelling recombinant proteins and preparation of insect cell culture media. Accordingly, this available reference is incorporated herein by reference.

The procedures for the cultivation of viruses and cells are described in L. E. Volkman and M. D. Summers, *J. Virol*, 19:820-832 (1975) and L. E. Volkman, M. D. Summers and C. H. Hsieh, *J. Virol*, 19:820-832 (1976). Viral growth kinetics were determined as described by L. E. Volkman, et al., supra. using *S. frugiperda* and a 1.5% agarose overlay.

THE INSECT SIGNAL SEQUENCE

The preferred DNA sequence isolated and cloned in the current invention encodes for a Lepidopteran *Manduca sexta* AKH signal peptide which has the following basic sequence:

5' ... ATG—TAC—AAG—CTC—ACA—GTC—TTC—CTG—
ATG—TTC—
Met—Tyr—Lys—Leu—Thr—Val—Phe—Leu—Met—Phe—

ATC—GCT—TTC—GTC—ATC—ATC—GCT—GAG—
GCC ... 3'
Ile—Ala—Phe—Val—Ile—Ile—Ala—Glu—Ala

It is believed that within the Order Lepidoptera, the AKH signal displays much greater homology than between other insect orders and therefore all DNA sequences coding for Lepidopteran AKH signal peptides are covered by this invention.

Of course, it is recognized by those skilled in the art that the DNA sequences may vary due to the degeneracy of the genetic code and codon usage. All DNA sequences which code for the AKH signal peptide amino acid sequences shown above are included in this invention. Additionally, it will be recognized by those skilled in the art that allelic variations may occur in the DNA sequences which will not significantly change the energy substrate metabolizing activity by the amino acid sequences of the proteins for which the DNA sequences code.

The DNA fragment containing the AKH signal gene can then be subcloned into the appropriate recombinant vector such as a plasmid or viral vector. Those skilled in the art will recognize that there are numerous possible vectors which may be utilized and even more numerous techniques for ligation into these recombinant vectors. The insect virus was a preferred recombinant vector in the current invention, with the baculovirus being most preferred. In the present invention the preferred baculovirus was the *Autographa californica* nuclear polyhedrosis virus, (AcMNPV), strain E2. Alternatively one could use the closely related and naturally occurring strains, *Trichoplusia ni* MNPV, *Rachiplusia ou* MNPV, *Galleria mellonella* MNPV and any plaque-purified strains such as the M3, R9, S1 and S3 strains of AcMNPV isolated and characterized in G. E. Smith and M. D. Summers, *J. Virol.*, 33:311-319 (1980), as well as *Bombyx mori* NPV (BmNPV).

The recombinant vector may then be used to infect or to transform an insect cell system, so that the AKH signal immediately precedes DNA coding for a desired gene product. As used herein, an insect cell system is comprised of an insect capable of being infected or transformed, or cell cultures or tissue cultures derived therefrom. This invention can therefore be employed using the conventional BEV system under the control of baculovirus late promoters, such as polyhedrin or 10K or can be utilized in stably-transformed cells expressing the desired protein product under the control of other baculovirus promoters, such as the IE1 immediate-early promoter or the 39K delayed-early promoter with or without the addition of transcriptional enhancer elements.

EXAMPLE I

Methodology for Insertion of the *Manduca Sexta* Adipokinetic Hormone Signal Sequence into the *Autographa Californica* Nuclear Polyhedrosis Virus The subject AKH signal sequence is employed to advantage using the following general strategy: A restriction endonuclease site within the coding region of the gene to be expressed is selected which is downstream from its native signal sequence cleavage site. This restriction site links the coding sequence of the mature polypeptide with the insect signal sequence. More particularly, a restriction site which is unique within the open reading frame, is as close as possible to the signal peptidase cleavage site, and produces a 5-prime or 3-prime protruding end is ideal. Two complementary single-stranded oligonucleotides are then synthesized which, when annealed, encode the insect signal sequence and the N-terminal sequence of the mature polypeptide up to the restriction site described above. The addition at the 5-prime end of the synthetic molecule of a sequence which is complementary to the cloning site of the target expression vector facilitates the assembly of the synthetic molecule, vertebrate gene, and expression vector.

A. Construction of Synthetic DNA Encoding the AKH Precursor Signal Peptide Sequence The following steps were utilized for synthesis of double strand DNA representing the signal peptide coding region of the Lepidopteran AKH signal.

1. The following signal peptide-coding, single-strand oligonucleotide was synthesized and purified by standard techniques of oligonucleotide synthesis:

5'   ATG-TAC-AAG-CTC-ACA-GTC-TTC-CTG-ATG-TTC-ATC-GCT-TTC-GTC-ATC-ATC-GCT-GAG-GCG 3'

2. A 15-oligonucleotide primer complementary to the coding strand was synthesized, and the two oligonucleotides were annealed:

5' ATG—TAC—AAG—CTC—ACA—GTC—TTC—CTG—
ATG—TTC—ATC—GCT—TTC—GTC—ATC—ATC—
GCT—GAG—GCG 3'
3' TAG—TAG—CGA—CTC—CGC 5'

3. The strand complementary to the large coding strand was completed enzymatically using the Klenow fragment of DNA polymerase I and deoxynucleoside triphophates:

5'   ATG-TAC-AAG-CTC-ACA-GTC-TTC-CTG-ATG-TTC-3'

TAC-ATC-TTC-GAG-TGT-CAG-AAG-GAC-
TAC-AAG-ATC-GCT-TTC-GTC-ATC-ATC-
GCT-GAG-GCG

3'
TAG-CGA-AAG-CAG-TAG-TAG-CGA-CTC-CGC
5'

4. Double strand DNA representing the complete signal peptide was phosphorylated and purified by gel exclusion chromatography:

Met[1] Tyr  Lys  Leu  Thr  Val  Phe
5' pATG—TAC—AAG—CTC—ACA—GTC—TTC—
3'  TAC—ATC—TTC—GAG—TGT—CAG—AAG—

Leu  Met  Phe  Ile  Ala  Phe  Val  Ile
CTG—ATG—TTC—ATC—GCT—TTC—GTC—ATC—
GAC—TAC—AAG—TAG—CGA—AAG—CAG—TAG—

Ile  Ala  Glu  Ala[19]
ATC—GCT—GAG—GCG 3'
TAG—CGA—CTC—CGCp 5'

B. Construction of a Baculovirus Transfer Vector for Expression of Foreign Genes Attached to the AKH Precursor Signal Peptide The strategy for attachment of foreign gene sequences to the AKH precursor signal peptide for baculovirus-directed expression was achieved by way of constructing a pVL941 vector containing the AKH signal code. The vector contains a unique BamHI site for insertion of a foreign gene sequence, wherein such foreign gene sequence has its own ATG translation and initiation codon which is followed by the DNA sequence for the signal peptide sequence for the protein which is to be secreted. In a preferred embodiment of the pVL941 vector, the non-translated leader sequence, −1 to −50 nucleotides is left intact along with a few additional nucleotides between the EcoRV site (approximately −98) and the transcription start (−50). Further, the −1 to −8 non-translated nucleotides need to be retained at the 5′ position relative to the translation initiation codon of ATG for any foreign gene being inserted. Similar vectors can be constructed using the pVL1393 and pVL1392 vectors with their respective multiple cassette cloning sites (See FIGS. 1, 2a and 2b). The procedure for constructing the signal peptide transfer vector is summarized as follows.

C. Selection and Preparation of Transfer Vector

Of several transfer vectors available for transferring the AKH coding region into AcMNPV genome, the preferred vector pVL941 was utilized because it has proven to result in high level expression of non-fused foreign proteins. A restriction endonuclease map of pVL941 is given in FIG. 1.

The preparation of pVL941 for insertion of the AKH coding region was as follows:

1 μg pVL941 was cleaved at the unique BamHI site:

```
---------GGATCC---------
---------CCTAGG---------
```

(see FIG. 1), by digestion with BamHI. The 5′ ends of the cleaved pVL941 were dephosphorylated with calf intestinal phosphatase to prevent recircularization as follows:

```
---------G        + HOGATCC---------
---------CCTAGOH           G---------
```

The two BamHI-cohesive ends were made blunt-ended with deoxynucleotide triphosphates and the Klenow fragment of DNA polymerase I:

```
---------GGATC    + HOGATCC---------
---------CCTAGOH    CTAGG---------
```

The blunt-ended transfer vector was ligated to the double-stranded AKH precursor signal peptide coding region. As a result, this construct has a new unique BamHI site:

```
            Met¹ . . . . . . . Ala¹⁹
---------GGATCATG ~ ~ ~ ~ ~ ~ ~ ~ GCGGATCC---------
---------CCTAGTAC ~ ~ ~ ~ ~ ~ ~ ~ CGCCTAGG---------
                                       |
                                  new unique BamHI site
```

The BamHI-digested, dephosphorylated, blunt-ended pVL941 vector was purified by electrophoresis in agarose gel. By digesting the construct with BamHI, removing the 5′ overhanging termini with mung bean nuclease, and dephosphorylating, the construct is ready to accept foreign gene sequences:

```
            Met¹ . . . . . . Ala¹⁹
---------GGATCATG ~ ~ ~ ~ ~ ~ ~ ~ GCG/////////////// C---------
---------CCTAGTAC ~ ~ ~ ~ ~ ~ ~ ~ CGC/////////////// G---------
....pVL941....|  .  AKH signal  .  |  ... foreign gene ... |...pVL941.
```

EXAMPLE II

Construction of CD4 cell surface protein T4) Expression Vectors Containing an Insect Signal Peptide In a most preferred embodiment, CD4 (T cell surface protein T4) expression vectors containing the Lepidopteran AKH signal DNA sequence were constructed. To construct a baculovirus expression vector in which the natural signal peptide of CD4 is replaced with the Lepidopteran AKH signal sequence, the signal peptide cleavage site on the CD4 precursor must be known. Because sequence data from naturally expressed CD4 in human cells is unavailable, the signal peptide cleavage site derived from recombinant CD4 expressed in vertebrate and insect cells was utilized. For soluble CD4 expressed in Chinese hamster ovary cells (R. A. Fisher et al., *Nature*, 331:76–78 (1988)) and *Spodoptera frugiperda* cells (R. E. Hussey et al., *Nature*, 331:78–81 (1988)), the amino terminus of the processed CD4 begins with the 26th amino acid of the open reading frame. A unique RsaI site located between amino acids 41 and 43 of the CD4 open reading frame was used to link the carboxy-terminal portion of the CD4 gene with synthetic oligonucleotides encoding an insect signal sequence and amino acids 27–41 of the CD4 precursor.

The synthetic portion of the chimeric CD4 was constructed as follows: Complementary single-stranded oligonucleotides encoding the Manduca adipokinetic hormone leader peptide were synthesized by standard phosphoramidite chemistry. A BamHI cohesive end at the five-prime terminus of each oligonucleotide pair was included for cloning purposes. Two complementary single-stranded oligonucleotides encoding amino acids 27–42 of the CD4 precursor (including the RsaI site mentioned above) were also synthesized. An EcoRI site was added at the 3-prime end for cloning purposes. The exemplary insect signal oligonucleotides were annealed to the synthetic CD4 portion by engineering a six-base overlap between the BamHI and EcoRI digested pUC18. After verifying that the insect sequence was correct by nucleotide sequence analysis, a 100 base pair BamHI-RsaI fragment containing the insect signal sequence and the 5-prime end of the mature CD4 gene was then isolated for each insect signal peptide derivative.

The plasmid pT4B (provided by R. Axel, Howard Hughes Medical Institute, Columbia University) which contains the entire open reading frame of the CD4 gene (P. J. Maddon et al., *Cell,* 42:93–104 (1985)), was then digested with RsaI and XhoII to release a 1.5 kb fragment encoding the carboxy-terminal portion of the CD4 gene. This CD4 fragment and the synthetic fragments described above were ligated in one step into BamHI digested pVL941. Recombinant plasmids containing the CD4 chimeric gene in the proper orientation were identified by restriction mapping. The hybrid signal peptide-CD4 construct after ligation into pVL941 (or pVL1392 or pVL1393 multiple cloning site vectors) were then transferred to the wild-type polyhedrin region after transfection by a double homologous recombination event as described in the conventional BEV procedures of M. D. Summers and G. E. Smith, Bulletin No. 1555, supra.

As disclosed herein, the preferred embodiment of this invention provides the Lepidopteran *Manduca sexta* tobacco hornworm adipokinetic hormone peptide signal sequence useful to enhance the baculovirus promoter controlled expression of foreign proteins in insect cells. However, other Lepidopteran AKH signal sequences can be employed to advantage since a great degree of homology exists among the Lepidopteran order with respect to the AKH signal.

Further modifications of the invention herein disclosed will occur to persons skilled in the art who have the benefit of this disclosure, and all such modifications are deemed to be within the spirit and scope of the invention as defined by the appended claims.

What is claimed is:

1. A purified, isolated DNA sequence comprising a DNA sequence coding for a signal peptide for a Lepidopteran *Manduca sexta* adipokinetic hormone precursor.

2. The DNA sequence of claim 1 wherein the DNA sequence is further defined as the following nucleotide sequence: ATG TAC AAG CTC ACA GTC TTC CTG ATG TTC ATC GCT TTC GTC ATC ATC GCT GAG GCC.

3. A purified DNA sequence coding for a signal peptide of the following amino acid sequence: Met-Tyr-Lys-Leu-Thr-Val-Phe-Leu-Met-Phe-Ile-Ala-Phe-Val-Ile-Ile-Ala-Glu-Ala.

* * * * *